US00PP23592P2

(12) United States Plant Patent
Kordes

(10) Patent No.: US PP23,592 P2
(45) Date of Patent: May 14, 2013

(54) CLIMBING ROSE PLANT NAMED 'KORUETROKO'

(50) Latin Name: *Rosa hybrida*
Varietal Denomination: KORuetroko

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 420 days.

(21) Appl. No.: 12/925,247

(22) Filed: Oct. 14, 2010

(51) Int. Cl.
*A01H 5/00* (2006.01)

(52) U.S. Cl.
USPC ..... Plt./114

(58) Field of Classification Search ..... Plt./114
See application file for complete search history.

*Primary Examiner* — Susan McCormick Ewoldt

(57) ABSTRACT

A new and distinct variety of rose with long lasting, novel salmon-red flowers, and attractive foliage with good disease resistance. It exhibits climbing growth with abundant flowers. The new variety propagates well rooting cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORuetroko'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a climbing rose plant which was discovered in a cultivated area in June, 2005. The new rose variety resulted from a naturally occurring mutation of unknown causation on a branch of 'KORtersen', an unpatented rose from the same breeder.

The new rose plant was asexually propagated for further evaluation. This new and distinctive rose variety is named 'KORuetroko'.

SUMMARY OF THE INVENTION

The new rose plant may be distinguished from the unpatented rose by the following combination of characteristics:

1. Common flower color of 'KORuetroko' is salmon red. Common flower color of 'KORtersen' is silvery pink.
2. Petal count of 'KORuetroko' is 175 on average. Average petal count of 'KORtersen' is 120.

The new and distinct rose plant was selected due to its:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORuetroko' from all other varieties of which we are aware.

As part of the rose development program, Tim-Hermann Kordes asexually propagated the mutation by grafting to seedling understocks and conducted evaluations and observations on the resulting plants in a controlled environment in Offenseth-Sparrieshoop, Germany. The resulting seedlings exhibited distinctive physical and biological characteristics. The first asexual propagation of 'KORuetroko' was done by budding to seedling understocks in August, 2005 at the inventor's nursery in Offenseth-Sparrieshoop, Germany.

This initial and other subsequent propagations conducted in controlled environments demonstrate that 'KORuetroko' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, flowers, leaves, and stems of 'KORuetroko'.

DETAILED BOTANICAL DESCRIPTION

The following is a description of 'KORuetroko', as observed growing in October, 2010 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORtersen', an unpatented rose variety from the same inventor.

CHART 1

| Characteristic | 'KORuetroko' | 'KORtersen' |
|---|---|---|
| Common flower color | Salmon red | Silvery pink |
| Flower diameter | 75 mm | 110 mm |
| Fragrance | Light | Strong |

Parent: 'KORtersen'.

Classification:

*Botanical classification.*—*Rosa hybrida*, 'KORuetroko'.

*Commercial classification.*—Climbing rose.

FLOWER AND FLOWER BUD

Blooming habit: Recurrent.

Flower bud:

*Size.*—Upon opening, 20 mm in length from base of receptacle to end of bud and 15 mm diameter at its widest point.

*Bud form.*—Short. Globular.

*Bud color.*—As sepals first unfold, bud color is Red Group 39B. When ¼ open, the upper surface of petals is Red Group 40C, and the lower surface is Red Group 48B.

*Sepals.*—Size: Average 35 mm long×8 mm wide. Shape: Sepals generally acuminate. Sepal apex is generally cirrose. Weak foliaceous appendages on three of the five sepals. Base is flat at union with receptacle. Quantity: Five. Margins: With stipitate glands. Surface texture: Inner side: Covered in fine hairs. Outer surface: Smooth. Stipitate glands are present. Color: Upper surface Yellow-Green Group 146B. Lower surface Yellow-Green Group 146A.

Receptacle:

*Surface.*—Smooth. With fine hairs.

*Color.*—Yellow-Green Group 144A.

*Shape.*—Funnel-shaped.

*Size.*—10 mm (h)×8 mm (w).

Peduncle:

*Surface.*—With fine hairs and stipitate glands.

*Length.*—35 mm average length.

*Diameter.*—3 mm average diameter.

*Color.*—Yellow-Green Group 144A.

*Strength.*—Moderate.

*Borne.*—Multiple flower buds per stem, generally 5 to 9.

Flower bloom:

*Fragrance.*—Light.

*Duration.*—On the plant 8-10 days. Long lasting. As a cut flower, 5 to 7 days. Senesced petals drop away cleanly.

*Size.*—Medium flowered garden rose. When open, the average flower diameter is 75 mm and the average flower height is 40 mm.

*Form.*—Shape of flower when viewed from the side: Upon opening, upper part: Flat. Upon opening, lower part: Flat. Open flower, upper part: Flattened convex. Open flower, lower part: Concave.

Color:

*Upon opening, petals.*—Outermost petals: Outer Side: Marginal zone: Red Group 52A. Middle and basal zones: Red Group 52C with intonations of White Group N155B. Inner Side: Red Group 52B. Innermost petals: Outer Side: Red Group 52C with intonations of White Group N155B throughout. Inner Side: Red Group 52A.

*Upon opening, basal petal spots.*—Basal petal spot, outermost petals: Outer Side: Green-Yellow Group 1B. Inner Side: Green-Yellow Group 1B. Basal petal spot, innermost petals: Outer Side: Yellow Group 2C. Inner Side: Yellow Group 2A.

*After opening, petals.*—Outermost petals: Outer Side: Red Group 52C with intonations of White Group N155B throughout. Inner Side: Red Group 52B. Innermost petals: Outer Side: Red Group 52B. Inner Side: Red Group 52B.

*After opening, basal petal spots.*—Basal petal spot, outermost petals: Outer Side: Yellow Group 11D. Inner Side: Yellow Group 11B. Basal petal spot, innermost petals: Outer Side: White Group N155B. Inner Side: White Group N155B. Variegations: None.

General tonality: On open flower Red Group 52B. No change in the general tonality at the end of the $10^{th}$ day. Afterwards, general tonality is Red Group 52C.

Petals:

*Petal count.*—Approximately 160-190 petals under normal conditions.

*Petal reflex.*—Petals reflex slightly.

*Petal edge.*—Crenate.

*Petal shape.*—Deltoid. Apex shape is obtuse. Shape of base is acute.

*Petal size.*—35 mm long; 25 mm wide.

*Thickness.*—Thin.

*Petal arrangement.*—Generally in a regular pattern with overlapping edges.

Petaloids: Present.

*Petaloid count.*—Average of 20-30 per flower.

*Petaloid edge.*—Entire.

*Petaloid texture.*—Smooth.

*Petaloid shape.*—Spatulate.

*Petaloid size.*—Petaloids are 10 mm long and 4 mm wide.

*Petaloid color.*—Color of inner side is Red Group 52A. Color of outer side is Red Group 52A.

Reproductive organs:

*Pistils.*—Approximately 25 present. Stigmas: Location: Slightly superior in position to anthers. Color: Gray-Orange Group 163C. Styles: Length: 8 mm long. Color: Gray-Orange Group 163D.

*Stamens.*—Approximately 15-25 on average and regularly arranged. Anthers: Size: 3 mm long. Color: Gray-Orange Group 174C. Pollen: Generally absent. Filaments: Color: Gray-Yellow Group 174C. Length: 6 mm.

THE PLANT

Plant growth: Moderate vigor. Climbing habit. When grown as a budded nursery plant the average plant height is 150 cm and the average plant width is 90 cm.

Stems:

*Stem color.*—Young wood: Yellow-Green Group 144A. Older wood: Yellow-Green Group 144A.

*Stem surface.*—Young wood: Smooth. Older wood: Smooth.

Prickles: Present.

*Incidence.*—35-50 per 10 cm of young stem. 25-35 per 10 cm of mature stem.

*Size.*—Average length: 6 mm.

*Color.*—Immature prickles: Gray-Red Group 182B. Mature prickles: Gray-Orange Group 173C. Senescing to Gray-Brown Group 199C.

*Shape.*—Concave.

*Anthocyanin.*—Color Gray-Red Group 182B.

Leaves and leaflets: Normally 7 leaflets on normal leaves in middle of the stem.

*Venation pattern*.—Pyramidal net pattern.
*Leaf size*.—125 mm (l)×95 mm (w).
*Quantity*.—Abundant.
*Texture*.—Upper side of leaflet: Semi glossy. Smooth. Under side of leaflet: Matte. Smooth.
*Color, mature foliage*.—Upper Leaf Surface: Green Group 137A. Lower Leaf Surface: Green Group 137C.
*Color, juvenile foliage*.—Upper Leaf Surface: Green Group 137A. Lower Leaf Surface: Green Group 137C.
*Anthocyanin intonation*.—Present. Location: Intonations present on juvenile leaf margins, developing leaves, peduncles, and stems. Color: Gray-Purple Group 183A.

Stipules:
*Size*.—15 mm long. 9 mm between the tips of the stipule. Main body of stipule 4 mm in width.
*Shape*.—Longitudinally flanged.
*Stipule color*.—Yellow-Green Group 144A. Anthocyanin: Gray-Red Group 182B.
*Presence of stipitate glands*.—Present on margins.
*Margins*.—Ciliated with stipitate glands.

Petiole:
*Length*.—25 mm.
*Diameter*.—2 mm.
*Petiole color*.—Yellow-Green Group 144A.
*Underneath*.—A few small prickles underneath.
*Stipitate glands*.—Limited numbers of stipitate glands on margins.

Petiole rachis:
*Length*.—45 mm.
*Diameter*.—2 mm.
*Color*.—Yellow-Green Group 144A. Anthocyanin present on juvenile tissue. Color: Gray-Red Group 182A.
*Margins*.—Ciliated with stipitate glands.
*Prickles*.—A few small prickles underneath.
*Stipitate glands*.—Limited numbers of stipitate glands on margins.

Leaflets:
*Size*.—Average size of the terminal leaflet is 60 mm (l)×30 mm (w).
*Shape*.—Ovate. Base: Ovate. Apex: Acute.
*Margins*.—Serrated.
*Texture*.—Leathery.

Hips/seed formation: None observed.

Winter hardiness: To date, the variety has been grown successfully in Zone 5.

Disease resistance: Above average resistance to Powdery mildew (*Sphaerotheca pannosa*) and blackspot (*Diplocarpon rosae*) diseases under normal growing conditions.

I claim:

1. A new and distinct variety of rose plant, as described and illustrated herein.

* * * * *

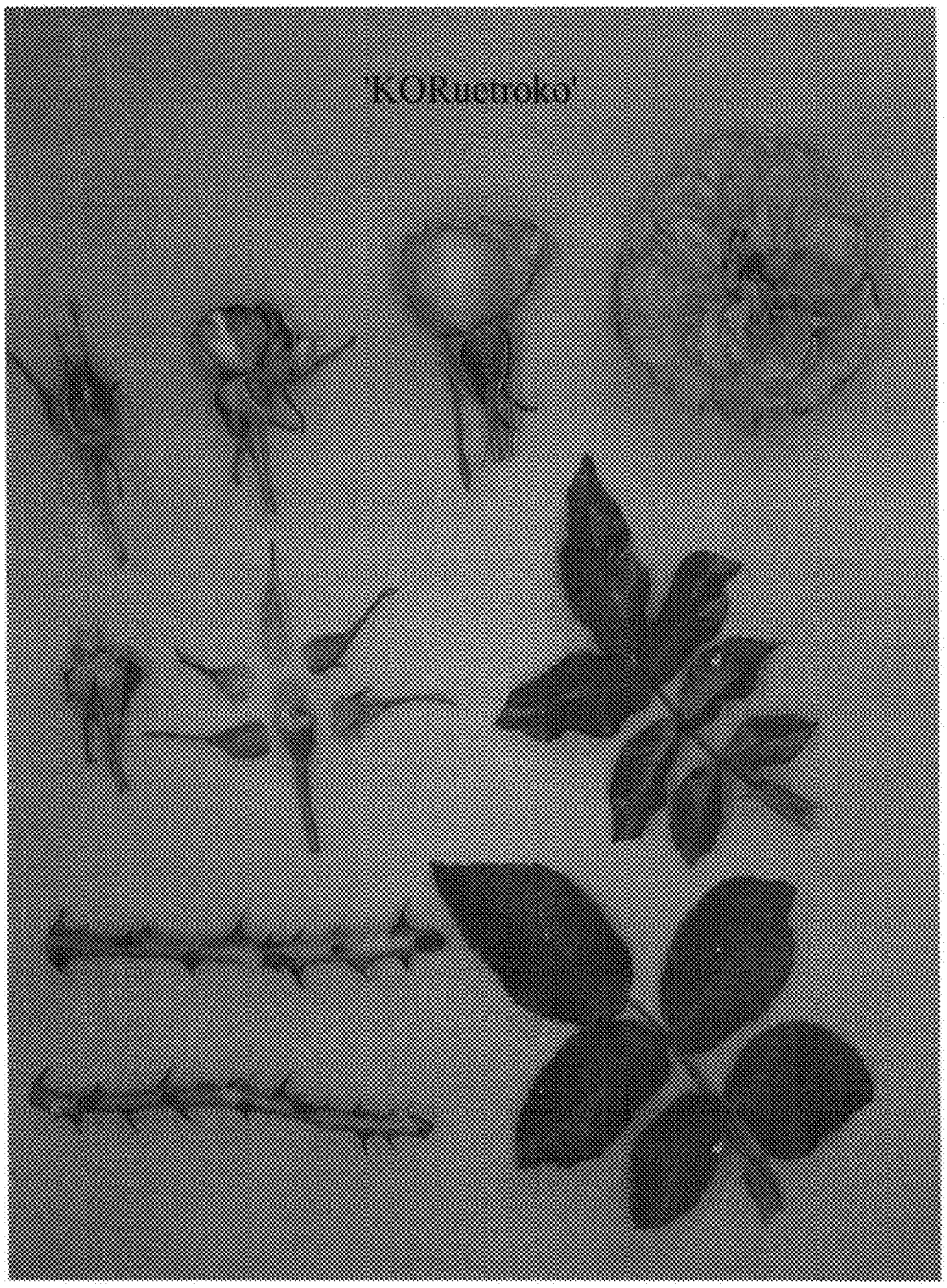
'KORuctroko'